United States Patent [19]

Osborn

[11] 4,202,352
[45] May 13, 1980

[54] APPARATUS FOR MEASUREMENT OF EXPIRED GAS CONCENTRATION IN INFANTS

[75] Inventor: John J. Osborn, Tiburon, Calif.

[73] Assignee: Research Development Corporation, San Francisco, Calif.

[21] Appl. No.: 894,170

[22] Filed: Apr. 6, 1978

[51] Int. Cl.² .............................................. A61B 5/08
[52] U.S. Cl. ................................................. 128/719
[58] Field of Search .................. 128/2.07, 2.08, 2 C, 128/719, 727, 728, 730; 73/123 R, 421.5 R

[56] References Cited

U.S. PATENT DOCUMENTS

| | | | |
|---|---|---|---|
| 3,659,590 | 5/1972 | Jones et al. ........................ 128/2.08 |
| 3,850,036 | 11/1974 | Sanctuary et al. ......... 73/421.5 R X |
| 3,896,792 | 7/1975 | Vail et al. ............................. 128/2.07 |
| 3,965,749 | 6/1976 | Hadden et al. ................. 73/421.5 R |

Primary Examiner—Kyle L. Howell
Attorney, Agent, or Firm—Flehr, Hohbach, Test, Albritton & Herbert

[57] ABSTRACT

Apparatus for measuring expired gas concentration in infants whose breathing rate is too high for normal analyzers by sampling the breath, for instance from the tube between the respirator and the infant, and drawing that sample of gas into an elongated, small diameter tube which serves to store the sample in a linear array substantially without intermixing. Several breaths are thus stored after which time the sampling may be interrupted and the stored gas drawn slowly through a gas analyzer.

10 Claims, 1 Drawing Figure

APPARATUS FOR MEASUREMENT OF EXPIRED GAS CONCENTRATION IN INFANTS

BACKGROUND OF THE INVENTION

In the treatment of infants with respiratory disease it can be of great importance to measure the concentration of carbon dioxide and oxygen in the expelled air of the infant. It is even more useful if these gases, particularly the carbon dioxide, can be measured at the end of expiration so as to obtain the highest carbon dioxide concentration of the expiration, usually called end-tidal peak carbon dioxide ($ECO_2$). Likewise, in the study of infants liable to "Sudden Infant Death Syndrome", the measurement of end-tidal peak carbon dioxide can be of critical importance because such infants may hypoventilate with a rising $ECO_2$ before going into apnea and dying.

In adults, who breathe at a rate of about 20 breaths per minute, it is relatively easy to take measurements of $ECO_2$. But most current rapid analyzers are limited in their response time to indicating only about 90% of the actual concentration in two tenths of a second. This means that in infants, who breath at a high rate, often over sixty or eighty, the response of a rapid gas analyzer is too slow to pick the peak of the end-tidal carbon dioxide because the next inspiration intervenes before the instrument has a chance to come to equilibrium for a valid measurement. Reliable measurements of end-tidal carbon dioxide in infants have heretofore only been possible using specially adapted mass-spectrometers which are very expensive and even then the end-tidal peak is often blurred by the rapid respiration rate.

Another problem in such measurement with respect to infants is that in order to measure, it is necessary to draw a continuous sample from the airway, typically at the rate of about 0.5 liters per minute and pass that volume through the gas analyzer. But in an infant who is only breathing one or two liters per minute and who is on the partially closed circuit of a ventilator, the half liter is a dangerously large amount to suck out of the airway.

SUMMARY OF THE INVENTION AND OBJECTS

The invention is incorporated in apparatus including means for sampling the gas from an infant's airway and simultaneously returning gas to that airway in the same volume so that there is no net loss of gas from the airway. Means are further provided to discontinue sampling of gas from the airway and thereafter direct the previously drawn sample to a gas analyzer at a relatively slow rate such that the analyzer may come to equilibrium and give valid measurements of end-tidal peak carbon dioxide.

It is, therefore, a general object of the present invention to provide an improved apparatus for measurement of expired gas concentration in infants.

It is a further object of the present invention to provide such an improved apparatus for measuring expired gas concentration in infants wherein accurate measurements can be taken with existing equipment and without subjecting the infant to the dangers of drawing large volumes of gases from the airway.

BRIEF DESCRIPTION OF THE DRAWING

The single FIGURE is a schematic diagram of apparatus for measurement of expired gas concentration in infants in accordance with the invention.

DETAILED DESCRIPTION OF THE PREFERRED EMBODIMENT

Figure 1:
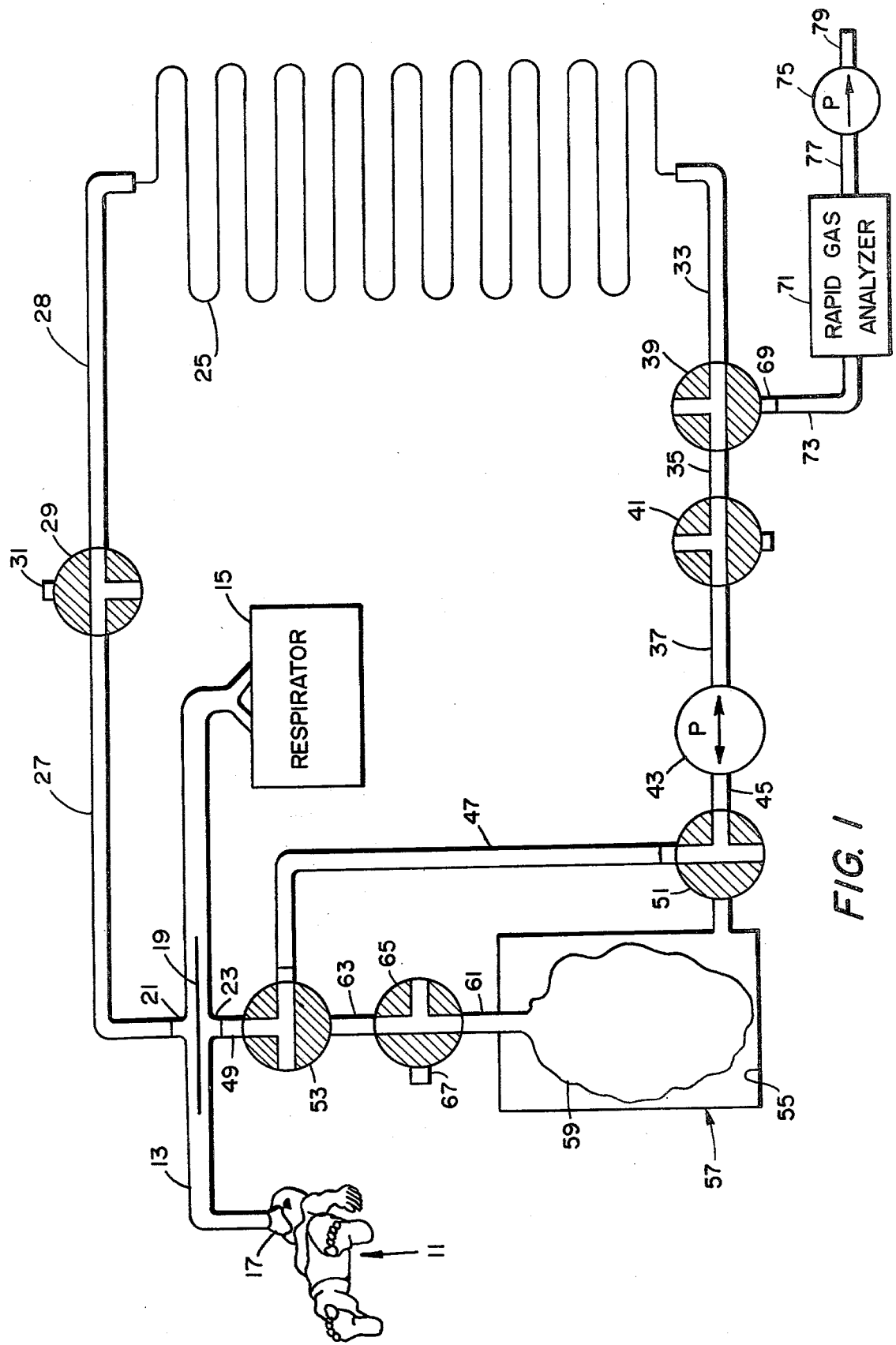

Referring to the FIGURE there is shown an infant 11 utilizing an airway 13 coupled to a respirator 15. The airway 13 may employ a face mask 17, as shown, or may include an intratracheal tube or the like. The airway 13 includes a baffle 19 extending longitudinally in the area of taps 21 and 23. The baffle 19 serves to isolate the tap 21 from the tap 23 whereby gases going to or from either will not interfere with the gas from the opposite tap.

The tap 21 is connected to a loop of fine tubing 25 through lines 27 and 28 and valve 29. Valve 29 includes an exhaust port 31 and when rotated counterclockwise from the position as shown will serve to connect loop 25 to the atmosphere through the port 31.

The opposite end of the loop 25 is connected by lines 33, 35 and 37 and valves 39 and 41 to a reversible pump 43. The opposite side of the pump 43 is connected to the tap 23 in the airway 13. As shown this route is defined by the lines 45, 47 and 49 together with the valves 51 and 53.

Alternatively, with the valves 51 and 53 rotated 90° clockwise and counterclockwise respectively, from the position shown, the pump 43 is connected to the outer chamber 55 of a captive bag assembly 57. The captive bag 59 of that assembly communicates with the tap 23 through the lines 61, 63 and 49 and the valves 65 and 53. The valve 65 includes an exhaust port 67 which communicates with the interior of the captive bag 59 when the valve 65 is rotated 90° clockwise from the position shown.

The valve 39 includes a port 69 which communicates with the loop 25 when the valve 39 is rotated 90° clockwise from the position shown. Tap 69 further communicates with a rapid gas analyzer 71 through the line 73. Gas from the loop 25 may be drawn through the rapid gas analyzer by means of a pump 75 connected to the analyzer 71 by the line 77. The discharge of the pump 75 may be vented to atmosphere through the line 79.

In the operation of the apparatus with the valves 51 and 53 set as shown in the drawing, the unit operates without using the captive air bag assembly 57. With the valves 29 and 39 set as shown in the drawing the apparatus is set for the first of two phases of operation. In this first phase, which lasts for several seconds or longer, the pump 43 operates to circulate gas from the airway 13 through the valve 31, the loop 25, the valve 39, the pump 43 itself, the valves 51 and 53 to the tap 23 of the airway 13. Phase one operates for a sufficiently long period of time to permit the infant to breath several breaths. The tube loop 25 is chosen to be long enough so that the transit time of a gas particle through it is longer than the time required for several breaths at the normal infant respiratory rate. Conveniently, this tube may be about 10 meters long with an internal diameter of 1 millimeter or less with the pump 43 operating at a rate of approximately one-half liter per minute.

Even though the pump draws a half liter of gas per minute from the airway 13 at the tap 21, the same amount of gas is being simultaneously returned to the airway through the tap 23. Consequently, there is no net loss of gas volume in the airway itself.

During the second phase of operation the valve 29 is rotated 90° counterclockwise from the position shown and valve 39 rotated 90° clockwise from the position shown. The pump 75 is then operated to draw the gas from the loop 25 slowly through the rapid gas analyzer 71. During this phase of operation measurements of gas concentrations are actually made and no gas is drawn from the airway 13. After sufficient time for the gas measurements to be made the system returns to phase one and the operation is repeated.

The apparatus then does not measure every breath of the infant but it does measure several breaths in sequence. If it were felt necessary to measure every breath, multiple apparatus of the type shown could be employed and phased in such a manner that when one is in the first phase of operation the other is in the second phase.

It may be considered advantageous to prevent mixing of the gases at inlet and outlet lines of the loop 25 and if this mode of operation is required the captive gas bag assembly 57 may be employed by rotating the valves 51 and 53 clockwise and counterclockwise respectively for 90°. The line 47 is then incapacitated and during phase one of the operation gas is drawn through the loop 25 by the pump 43 and, rather than being returned to the airway tap 23, is directed to the outer chamber 55 of the assembly 57. During this time gases within the bag 59 are thus forced through the valves 65 and 53 to the tap 23.

During the second phase of operation, gases from the loop 25 are drawn through the gas analyzer in the same fashion as during phase two of the first described mode of operation. However, when the captive bag assembly 57 is employed pump 43 is also utilized during the second phase to refill the bag 59. Thus during phase two of the operation utilizing the assembly 57, valves 41 and 65 are rotated 90° counterclockwise and clockwise respectively and atmospheric air, or if desired some other gas, is drawn into the captive bag 59. When phase one recommences, the valves 41 and 65 are returned to their original position and the pump 43 is again operated in its forward direction.

Thus it is seen that the invention comprises apparatus whereby gas can be sampled from the airway and simultaneously returned to that airway in the same volume so that there is no net loss of gas volume from the airway. A conventional rapid gas analyzer can then be given adequate time to equilibriate and make a valid measurement of $ECO_2$ in spite of the rapid respiration of the infant.

An important aspect of the invention is the utilization of a very small internal diameter tube for the loop 25 such that when gas is drawn through the loop at a reasonable rate the flow is laminar with very little mixing of the gas. With this construction, if a gas of an undulating concentration is drawn into the loop 25 it remains in that undulating concentration throughout the length of the loop 25. The concentration of gas flowing from the opposite end of the loop will undulate in approximately the same wave form as it is admitted to the loop with very little slurring or mixing. It may be said then that the gases from the airway 13 are stored in analog form throughout the length of the loop 25.

What is claimed is:

1. In an apparatus for measuring expired gas concentrations of a patient, an airway adapted to be placed in communication with the patient's respiratory system, pump means having its intake connected to said airway for drawing a predetermined volume of gas therefrom to be sampled, a captive bag assembly having an outer chamber and a captive bag within said outer chamber, the interior of said captive bag defining an inner chamber, the exhause of said pump means being connected to one of said chambers and the other of said chambers being connected to said airway whereby the captive bag assembly replenishes the gas to the airway in the same predetermined volume and simultaneously with the operation of said pump means to draw gas therefrom.

2. Apparatus as defined in claim 1 wherein said airway includes first and second taps, the intake of said pump means being connected to said first tap, said one of said chambers being connected to said second tap, and baffle means disposed in said airway between said taps for isolating the same.

3. Apparatus as defined in claim 1 wherein said airway includes an elongated tube having an internal diameter sufficiently small in consideration of pumping capacity of said pump means to provide laminar flow therethrough and a length sufficiently great, compared to the lung volume and respiration rate of the patient, that the transit time of a gas particle through the tube is greater than the time required for several breaths of the patient.

4. Apparatus as defined in claim 3 wherein said elongated tube has an internal diameter no greater than 1 mm. and a length of approximately 10 meters, said pump means having a pumping capacity of about 0.5 liter per minute.

5. In an apparatus for measuring expired gas concentrations of an infant, an airway adapted to be placed in communication with the infant's respiratory system, an elongated tube, pump means in communication with said elongated tube for pumping respiratory gas therethrough, a gas analyzer, valve means having a first position placing said elongated tube in communication with said airway whereby gases from the respiratory system of the infant may be drawn into said elongated tube by said pump means, said valve means having a second position placing said elongated tube in communication with said gas analyzer whereby gases previously drawn into said elongated tube while the valve means was in its first position may be analyzed when said valve means is in its second position.

6. Apparatus as defined in claim 5 wherein said elongated tube has an internal diameter sufficiently small in consideration of the pumping capacity of said pump means to provide laminar flow therethrough and a length sufficiently grea, compared to the lung volume and respiration rate of the infant, that the transit time of gas particle through the tube is greater than the time required for several breaths of the infant.

7. Apparatus as defined in claim 6 wherein said elongated tube has an internal diameter no greater than 1 mm. and a length of approximately 10 meters, and pump means having a capacity of about 0.5 liter per minute.

8. Apparatus as defined in claim 5 wherein said pump means includes means for drawing a predetermined volume of gas from said airway through elongated tube when said valve means is in its first position, together with replenish means coupled to said airway for replenishing gas therein in the same predetermined volume and at the time said valve means is in its first position.

9. Apparatus as defined in claim 8 wherein said replenish means comprises a captive bag assembly having an outer chamber and a captive bag within said outer chamber, the interior of said captive bag defining an inner chamber, one of said chambers being in communication with said airway and the other of said chambers being in communication with said elongated tube when said valve means is in its first position.

10. Apparatus for measuring expired gas concentrations of a patient comprising pumping means adapted to be placed in communication with the airway of the patient for drawing a sample of the patient's respiratory gases, storage means in communication with said pumping means for storing the drawn respiratory gases in a sequence corresponding to the sequence that the gases are expired by the patient, a gas analyzer for analyzing said gases and valve means for interrupting the communication between said storage means and the airway of the patient and for simultaneously placing said storage means in communication with said gas analyzer.

* * * * *